(12) United States Patent
Stebbins et al.

(10) Patent No.: US 12,396,941 B2
(45) Date of Patent: Aug. 26, 2025

(54) COSMETIC COMPOSITION THAT RESISTS PILLING

(71) Applicant: L'OREAL, Paris (FR)

(72) Inventors: Nicholas David Stebbins, Clark, NJ (US); David Chan, Edison, NJ (US)

(73) Assignee: L'OREAL, Paris (FR)

( * ) Notice: Subject to any disclaimer, the term of this patent is extended or adjusted under 35 U.S.C. 154(b) by 135 days.

(21) Appl. No.: 17/387,982

(22) Filed: Jul. 28, 2021

(65) Prior Publication Data
US 2023/0046148 A1    Feb. 16, 2023

(51) Int. Cl.
| | |
|---|---|
| A61K 8/81 | (2006.01) |
| A61K 8/06 | (2006.01) |
| A61K 8/19 | (2006.01) |
| A61K 8/34 | (2006.01) |
| A61K 8/365 | (2006.01) |
| A61K 8/37 | (2006.01) |
| A61K 8/39 | (2006.01) |
| A61K 8/42 | (2006.01) |
| A61K 8/49 | (2006.01) |
| A61K 8/55 | (2006.01) |
| A61K 8/73 | (2006.01) |
| A61Q 19/00 | (2006.01) |

(52) U.S. Cl.
CPC ............ *A61K 8/8164* (2013.01); *A61K 8/062* (2013.01); *A61K 8/19* (2013.01); *A61K 8/342* (2013.01); *A61K 8/347* (2013.01); *A61K 8/365* (2013.01); *A61K 8/37* (2013.01); *A61K 8/39* (2013.01); *A61K 8/42* (2013.01); *A61K 8/4926* (2013.01); *A61K 8/553* (2013.01); *A61K 8/73* (2013.01); *A61K 8/8147* (2013.01); *A61K 8/8158* (2013.01); *A61Q 19/00* (2013.01); *A61K 2800/48* (2013.01)

(58) Field of Classification Search
CPC .................................................. A61K 8/8164
See application file for complete search history.

(56) References Cited

U.S. PATENT DOCUMENTS

| | | | |
|---|---|---|---|
| 7,108,860 B2* | 9/2006 | Dueva | A61Q 17/04 424/59 |
| 7,780,971 B2* | 8/2010 | Chevalier | A61K 8/88 424/78.03 |
| 2007/0020213 A1 | 1/2007 | Tamarkin et al. | |
| 2014/0335136 A1* | 11/2014 | Brieva | A61K 8/0241 424/59 |
| 2016/0158261 A1 | 6/2016 | Friedman et al. | |
| 2017/0119644 A1* | 5/2017 | White | A61K 8/062 |

FOREIGN PATENT DOCUMENTS

| | | | | |
|---|---|---|---|---|
| EP | 2832742 A1 * | 2/2015 | | A61K 8/64 |
| FR | 2822375 A1 | 9/2002 | | |
| WO | WO-2016106333 A1 * | 6/2016 | | A61K 8/06 |

OTHER PUBLICATIONS https://www.products.pcc.eu/en/inci-names/laureth-4-phosphate/ (Year: 2023).*
https://cosmetics.specialchem.com/inci-ingredients/acrylates-beheneth-25-methacrylate-copolymer#:~:text=Acrylates%2FBeheneth%2D25%20Methacrylate%20Copolymer%20is%20a%20copolymer%20of%20the,an%20aqueous%20viscosity%20increasing%20agent. (Year: 2023).*
https://www.biosynth.com/p/GCA03958/56039-58-8-benzylidene-camphor-sulfonic-acid (Year: 2023).*
https://cosmetics.specialchem.com/inci-ingredients/laureth-4#:~:text=To%20enhance%20the%20texture%20and,works%20as%20an%20antistatic%20agent. (Year: 2014).*
Date proof for cosmetics.specialchem.com (Year: 2014).*
https://www.seppic.com/en/montanov-68mb#:~:text=O%2FW%20alkylpolyglucoside%20emulsifier%20of,TEWL)%20and%20the%20moisturizing%20effect. (Year: 2020).*
https://blog.essentialwholesale.com/cosmetic-thickeners-and-natural-polymers/#:~:text=Xanthan%20gum%20is%20widely%20used,hazy%20but%20neutral%20pH%20solution. (Year: 2019).*
Date proof for cosmetics.specialchem.com (laureth-4) (Year: 2014).*
Wayback for seppic.com (Year: 2020).*
cosmetics.specialchem.com (oleth-10) (Year: 2014).*
Date proof for cosmetics.specialchem.com (oleth-10) (Year: 2014).*
Anonymous, Mintel, "Day Pore Minimizer", Feb. 17, 2009, XP055943580, No. 1073484, www.gnpd.com.
Anonymous, Mintel, "Vitamin-Infused Cleansing Emulsion", Jan. 26, 2018, XP055943586, No. 5344131, www.gnpd.com.
Anonymous, Mintel, "Revitalizing Emulsion—Face, Eyes, Neck", Dec. 6, 20119, XP055943619, No. 1686363 www.gnpd.com.
Search Report issued to French counterpart Application No. FR2111499 dated Aug. 30, 2022.

* cited by examiner

*Primary Examiner* — Brian-Yong S Kwon
*Assistant Examiner* — Danielle Kim
(74) *Attorney, Agent, or Firm* — McNees Wallace & Nurick LLC

(57) ABSTRACT

A pilling-resistant cosmetic composition is in the form of an oil in water emulsion that includes a water phase and an oily phase, and includes at least one cosmetically acceptable polymeric thickener selected from the group consisting of crosspolymers, gums, taurate based polymers, carbomers, polyacrylates, and combinations thereof, at least one ethoxylated agent in liquid form at ambient temperature in a range from about 20° C. to about 28° C. and has an HLB from about 8.5 to about 16; and at least one oil. The pilling-resistant cosmetic composition resists pilling when applied by rubbing or smoothing on a keratinous substrate.

20 Claims, No Drawings

COSMETIC COMPOSITION THAT RESISTS PILLING

FIELD OF THE INVENTION

The present invention is generally directed to a pilling-resistant cosmetic composition and method for manufacturing the same for providing benefits to the skin of a user, the pilling-resistant cosmetic composition including a high amount of actives for conferring benefits to the user's skin and having a favorable textural aesthetic that is resistant to pilling that is associated with use of polymeric thickeners and other ingredients that stabilize and lend aesthetic benefits to the pilling-resistant cosmetic composition. Benefits of the pilling-resistant cosmetic composition may include, but are not limited to, generally moisturizing skin, or enhancing skin, for example, by improving skin smoothness and radiance, minimizing pore appearance, reducing the appearance fine lines and wrinkles, brightening skin, treating acne, or reducing the effects of acne, and reducing one or more of dryness, tightness, dark spots, redness, and inflammatory lesions, or a combination of any of these.

BACKGROUND OF THE INVENTION

There are a variety of skin conditions that benefit from leave-on cosmetic compositions that may be applied on the skin for any of a variety of possible benefits. In some examples, it is challenging to formulate skin care cosmetics that include sufficiently high amounts of actives to confer desired benefits. Products that include high amounts of actives are often formulated with a high content of oils, emulsifiers and/or thickeners to facilitate dispersion and/or solubilization of the actives. Such formulations can be heavy and leave a greasy skin feel or cause dryness or irritation, and those that include stabilizing thickeners are vulnerable to pilling. More generally, skin care compositions in emulsion forms with about forty percent or more water phase that include polymeric thickeners can also be vulnerable to pilling on application. Such pilling can affect the availability of the actives for maximum benefit to the skin, and pilling is particularly problematic for leave on formulations.

Accordingly, there is a need in the art for a cosmetic composition that offers light weight feel in a stable formulation that resists pilling typically associated with thickener stabilized compositions.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

In various embodiments, a composition is provided for use according to the invention that includes a direct fluid emulsion composition and method for manufacturing the same for conferring benefits to the user's skin. The disclosed pilling-resistant cosmetic composition has a favorable textural aesthetic that is resistant to pilling associated with use of polymeric thickeners and includes ingredients that stabilize and lend aesthetic benefits to the pilling-resistant cosmetic composition. The pilling-resistant cosmetic composition is in the form of a direct emulsion (oil in water or silicone in water) includes a polymeric thickener ethoxylated emulsifier agent stabilizing system, wherein the pilling-resistant cosmetic composition does not exhibit appreciable or any pilling on application and is generally stable from any phase separation or gellifying and retains a smooth, lightweight texture. The pilling-resistant cosmetic composition may be provided in a lotion, serum, cream, or other suitable direct emulsion form.

The pilling-resistant cosmetic composition in the form of a direct oil in water emulsion includes water and oily phases. In some embodiments, the water phase is present in an amount that is at least about 40% or more based on the total weight of the pilling-resistant composition.

In some embodiments, the pilling-resistant cosmetic composition is an oil in water emulsion comprising a water phase and an oily phase, the pilling-resistant cosmetic composition comprising: at least one cosmetically acceptable polymeric thickener selected from the group consisting of crosspolymers, gums, taurate based polymers, carbomers, polyacrylates, and combinations thereof; at least one ethoxylated agent in liquid form at ambient temperature in a range from about 20° C. to about 28° C. and has an HLB from about 8.5 to about 16; and at least one oil, wherein the pilling-resistant cosmetic composition resists pilling when applied by rubbing or smoothing on a keratinous substrate.

In some embodiments, the pilling-resistant cosmetic composition includes at least one cosmetically acceptable polymeric thickener is selected from the group consisting of polyacrylate crosspolymer-6, xanthan gum, hydroxyethyl acrylate/sodium acryloyldimethyl taurate copolymer, acrylamide/sodium acryloyldimethyltaurate copolymer, carbomer, ammonium acryloyldimethyltaurate/steareth-25 methacrylate crosspolymer, acrylates/beheneth-25 methacrylate copolymer, acrylates/C10-30 alkyl acrylate crosspolymer, ammonium polyacryloyldimethyl taurate, sodium polyacrylate, sclerotium gum, acrylamide/sodium acryloyldimethyltaurate copolymer (and) isohexadecane (and) polysorbate 80, and combinations thereof.

In some embodiments, the pilling-resistant cosmetic composition includes at least one cosmetically acceptable polymeric thickener is a gum selected from the group consisting of sclerotium gum, xanthan gum, cellulose gum, locust bean gum, carrageenan, and combinations thereof.

In some embodiments, the pilling-resistant cosmetic composition includes at least one ethoxylated agent is selected from the group consisting of ethoxylated fatty alcohols, ethoxylated fatty acids, and combinations thereof.

In some embodiments, the pilling-resistant cosmetic composition includes at least one ethoxylated agent is selected from the group consisting of (i) an laureth-x, where x is from 4 to about 12; (ii) an oleth-x, where x is from 5 to about 12; (iii) an PEG-X laurate where X is from 4 to about 12; (iv) an PEG-X isostearate where X is from 5 to about 12; (v) an PEG-X oleate where X is from 5 to about 12; and combinations thereof.

In some embodiments, the pilling-resistant cosmetic composition includes at least one ethoxylated agent is selected from the group consisting of laureth-4, oleth-10, and combinations thereof.

In some embodiments, the pilling-resistant cosmetic composition includes at least one oil is selected from the group consisting of octyldodecanol, glycine soja (soybean) oil, hydrogenated lecithin, isononyl isononanoate, isocetyl stearoyl stearate, dicaprylyl ether, isopropyl lauroyl sarcosinate, dicaprylyl carbonate, and combinations thereof.

In some embodiments, the pilling-resistant cosmetic composition includes at least one oil is selected from the group consisting of octyldodecanol present in a range from about 0.5% to about 3.5; cetearyl ethylhexanoate (and) isopropyl myristate present in a range from about 0.5% to about 2%; hydrogenated lecithin present in a range from about 0.1% to about 1%; isononyl isononanoate present in a range from about 1% to about 5%; isopropyl lauroyl sarcosinate present in a range from about 0.5% to about 2%; dicaprylyl carbonate present in a range from about 0.5% to about 1.5%; and combinations thereof, all amounts, by weight, based on the weight of the total composition.

In some embodiments, the pilling-resistant cosmetic composition includes at least one oil is selected from the group consisting of octyldodecanol present at about 2.4%; cetearyl ethylhexanoate (and) isopropyl myristate present at about 1.5%; hydrogenated lecithin present at about 0.3%; isononyl isononanoate present at about 2.0%; isopropyl lauroyl sarcosinate present at about 1.0%; dicaprylyl carbonate present at about 1.0%; and combinations thereof, all amounts, by weight, based on the weight of the total composition.

In some embodiments, the pilling-resistant cosmetic composition includes one or more ingredients selected from the group consisting of water-soluble solvents, at least one powder present in either the water or the oily phase, one or more additives present in either the water or the oily phase, and combinations thereof.

In some embodiments, the pilling-resistant cosmetic composition includes at least one powder, wherein the at least one powder is selected from the group consisting of silica, pigments, boron nitride, lauroyl lysine, perlite, talc, clays, cellulose, and combinations thereof.

In some embodiments, the pilling-resistant cosmetic composition includes the water phase present in an amount that is at least about 40% or more, based on the total weight of the pilling-resistant composition.

In some embodiments, the pilling-resistant cosmetic composition includes the oily phase present in an amount that is not greater than about 40%, based on the total weight of the pilling-resistant composition.

In some embodiments, the pilling-resistant cosmetic composition includes the ethoxylated agent comprises laureth-4, the pilling-resistant cosmetic composition optionally further comprises C14-22 alcohols (and) C12-20 alkyl glucoside.

In some embodiments, the pilling-resistant cosmetic composition includes the at least one ethoxylated agent in liquid form at an ambient temperature of about 25° C.

In some embodiments, invention provides a pilling-resistant cosmetic composition in the form of an oil in water emulsion, comprising: at least one polymeric thickener selected from the group consisting of polyacrylate crosspolymer-6, xanthan gum, hydroxyethyl acrylate/sodium acryloyldimethyl taurate copolymer acrylamide/sodium acryloyldimethyltaurate copolymer, carbomer, ammonium acryloyldimethyltaurate/steareth-25 methacrylate crosspolymer, acrylates/beheneth-25 methacrylate copolymer, acrylates/C10-30 alkyl acrylate crosspolymer, ammonium polyacryloyldimethyl taurate, sodium polyacrylate, sclerotium gum, acrylamide/sodium acryloyldimethyltaurate copolymer (and) isohexadecane (and) polysorbate 80, and combinations thereof; at least one ethoxylated agent in liquid form at ambient temperature in a range from about 20° C. to about 28° C. and has an HLB from about 8.5 to about 16; and at least one oil, wherein the pilling-resistant cosmetic composition resists pilling when applied by rubbing or smoothing on a keratinous substrate.

In some embodiments, the pilling-resistant cosmetic composition includes the at least one polymeric thickener present in a total amount or polymeric thickener in a range from about 0.4% to about 3%, by weight, based on the total weight of the pilling-resistant cosmetic composition, and wherein the at least one ethoxylated agent is present in a total amount or ethoxylated agent in a range from about 0.2% to about 5%, by weight, based on the total weight of the pilling-resistant cosmetic composition.

In some embodiments, the invention provides a pilling-resistant cosmetic composition in the form of an oil in water emulsion, comprising: at least one cosmetically acceptable polymeric thickener present in a total amount or polymeric thickener in a range from about 0.4% to about 3%, by weight, based on the total weight of the pilling-resistant cosmetic composition; at least one ethoxylated agent in liquid form at ambient temperature in a range from about 20° C. to about 28° C. and has an HLB from about 8.5 to about 16, present in a total amount or ethoxylated agent in a range from about 0.2% to about 5%, by weight, based on the total weight of the pilling-resistant cosmetic composition; and at least one oil, wherein the pilling-resistant cosmetic composition resists pilling when applied by rubbing or smoothing on a keratinous substrate.

In some embodiments, the pilling-resistant cosmetic composition includes the at least one cosmetically acceptable polymeric thickener is selected from the group consisting of crosspolymers, gums, taurate based polymers, carbomers, polyacrylates, and combinations thereof.

In some embodiments, the pilling-resistant cosmetic composition includes the at least one ethoxylated agent is selected from the group consisting of (i) an laureth-x, where x is from 4 to about 12; (ii) an oleth-x, where x is from 5 to about 12; (iii) an PEG-X laurate where X is from 4 to about 12; (iv) an PEG-X isostearate where X is from 5 to about 12; (v) an PEG-X oleate where X is from 5 to about 12; and combinations thereof.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

In the context of the invention, a direct emulsion is an oil in water emulsion.

As used herein, the term "pilling" refers to failure of some or all of a composition to soak in when applied to a keratinous substrate, including facial and body skin, lips, hair, and nails, forming small globules, strands or particles that collect on the surface, and exhibit an inability to be spread as a uniform emulsion. Instability can occur in compositions made outside of the scope of the disclosure (i.e., compositions lacking the disclosed polymer and ethoxylated agents), and compositions including amounts of polymeric thickener in excess of the amounts according to the disclosure. Likewise, other instability issues of a composition outside of the scope of the disclosure (i.e., compositions lacking the disclosed polymer and ethoxylated agents) include separation of phases; watery texture; gellification of the cosmetic composition.

The terms "Exclude," "Free" and "Essentially Free" means that no reliably measurable excluded material, for example, an excluded gellan and other gellifying agents, waxes, plant butters greater than about 5%, by weight, based on the total weight of the pilling-resistant cosmetic composition, and saturated fatty alcohols/acids above C16 present in amounts greater than about 5%, by weight, based on the total weight of the pilling-resistant cosmetic composition, or other excluded material as described herein, is present in the pilling-resistant cosmetic composition. The term "essentially free" means that, while it is preferred that no excluded material is present in the pilling-resistant cosmetic composition, it is possible to have very small amounts of the excluded material in the pilling-resistant cosmetic composition of the invention, provided that these amounts do not materially affect the advantageous properties of the pilling-resistant cosmetic composition. In particular, "essentially free" means that excluded material can be present in the pilling-resistant cosmetic composition at an amount of less than 5%, or less than 4%, or less than 3%, or less than 2%, or less than 1%, or less than 0.1% by weight, based on the total weight of the pilling-resistant cosmetic composition.

As shown herein, the inventors have provided the pilling-resistant cosmetic composition in the form of a direct oil in water emulsion that includes water and oily phases and includes at least one cosmetically acceptable polymeric thickener selected from the group consisting of crosspolymers, gums, taurate based polymers, carbomers, polyacrylates, and combinations thereof, at least one ethoxylated agent in liquid form at ambient temperature in a range from about 20° C. to about 28° C. and has an HLB from about 8.5 to about 16; and at least one oil. The pilling-resistant cosmetic composition resists pilling when applied by rubbing or smoothing on a keratinous substrate.

The pilling-resistant cosmetic composition may also include one or more additional ingredients selected from, but not limited to, phenylethyl resorcinol, chelating agents, other skin active components, antimicrobials and preservatives, fillers, antioxidants, fragrances, pearlescent agents, odor absorbers, coloring materials, essential oils, vitamins, and combinations of these.

A key problem in cosmetic compositions that include polymeric emulsifiers and thickeners is pilling resulting in the inability of a composition to be spread as a uniform emulsion resulting in failure of some or all of the applied composition to soak into skin. Pilling represents the formation of small globules or particles that collect on the skin's surface when the composition is spread on to a substrate, such as skin. Pilling is visually and aesthetically unpleasant and also adversely affects the effectiveness of the composition. Pilling is often associated with the presence of relatively high amounts of thickeners/thickening emulsifiers which are useful for stabilizing high amounts of skin actives. Although thickeners/thickening emulsifiers can be effective at stabilizing emulsions, the potential of pilling is high, even at modest usage levels of these ingredients. Moreover, for certain formulas, especially those with any electrolytes or ionic components, a higher level of polymer is required to afford stability increasing the risk of pilling. Pilling is an unacceptable trait for products, as consumers do not want their product to slough off of their skin; this issue becomes more pronounced as consumers layer more and more skin care and makeup products on their face.

The inventors sought to develop a solution for reducing pilling potential associated with a wide variety of polymeric thickeners. The inventors have surprisingly found that ethoxylated fatty alcohols and ethoxylated fatty acids represent a class of raw materials (herein referred to as "ethoxylated agents") that can significantly reduce pilling potential of multiple classes of polymeric thickeners/thickening emulsifiers that are used in a wide range of oil-in-water emulsions. In the general cosmetic arts, ethoxylated fatty alcohols and ethoxylated fatty acids are known as emulsifiers or as solubilizers and are characterized by the presence of a hydrophobic alky fatty alcohol/acid portion and a hydrophilic ethylene oxide portion.

In preparing the inventive pilling-resistant cosmetic composition, several liquid emulsifiers/solubilizers of intermediate HLB (from about 8- to about 16) were tested as additives to simplex formulas containing polymeric thickeners present in amounts that are known to result in pilling of the simplex formulas. Without being bound by theory, it is believed that an intermediate HLB emulsifiers (vs. an oil, for example) would interact with the water and oily emulsion components of the pilling-resistant cosmetic composition at the hydrophobic/hydrophilic interface and not at only one of the hydrophobic or hydrophilic portions of the agent. Lower HLB emulsifiers were not tested, as they are known in the art to make inverse emulsions and could disrupt and or destabilize direct emulsions. Ethoxylated agents selected from ethoxylated fatty alcohols and ethoxylated fatty acids were employed according to the disclosure and were shown to reduce or eliminate pilling in the simplex formulas that were otherwise known to pill. These test formulas did not result in inverse emulsions and/or destabilized direct emulsions. Specific examples of these ethoxylated agents, as shown in the examples, include laureth-4, oleth-10.

As shown, in some embodiments, the pilling-resistant cosmetic composition may optionally include one or more glyceryl containing ingredients, for example, but not limited to, polyglyceryl-6 dicaprate, and PEG-7 glyceryl cocoate, which may be advantageously used for enhancing permeability of actives, among other possible benefits.

Thus, the inventors have shown that ethoxylated agents employed as described and exemplified herein surprisingly demonstrate a marked effect of reducing pilling that has been a vexing problem in the art for a wide range of emulsion architectures that include a wide variety of polymeric thickeners. There is no evidence in the current art of any association of ethoxylated agents with the elimination and/or reduction of pilling associated with polymeric thickeners/thickening emulsifiers. The inventors have shown herein that a direct emulsion cosmetic composition that has potential to pill on the skin (caused by polymeric thickeners/thickening emulsifiers) can be improved by reduction or elimination of pilling upon inclusion of ethoxylated agents as disclosed herein.

In accordance with the various embodiments, it is contemplated that some or all of following ingredients would be excluded from the pilling-resistant cosmetic compositions used according to the invention: gellan and other gellifying agents, waxes, plant butters greater than about 5%, by weight, based on the total weight of the pilling-resistant cosmetic composition, and saturated fatty alcohols/acids above C16 present in amounts greater than about 5%, by weight, based on the total weight of the pilling-resistant cosmetic composition.

Accordingly, in various embodiments, the pilling-resistant cosmetic composition is provided according to the following detailed description.

Polymeric Thickeners (Polymers)

In accordance with the disclosure, the pilling-resistant cosmetic composition includes at least one cosmetically acceptable polymeric thickener. In some embodiments, the at least one polymeric thickener expressly excludes gellan.

In some embodiments, the least one cosmetically acceptable polymeric thickener is selected from the group consisting of crosspolymers, gums, taurate based polymers, carbomers, polyacrylates, and combinations thereof.

In some embodiments, the at least one cosmetically acceptable polymeric thickener is a gum selected from the group consisting of sclerotium gum, xanthan gum, cellulose gum, locust bean gum, carrageenan, and combinations thereof.

In some embodiments, the least one cosmetically acceptable polymeric thickener is selected from the group consisting of polyacrylate crosspolymer-6, xanthan gum, hydroxyethyl acrylate/sodium acryloyldimethyl taurate copolymer acrylamide/sodium acryloyldimethyltaurate copolymer, carbomer, ammonium acryloyldimethyltaurate/steareth-25 methacrylate crosspolymer, acrylates/beheneth-25 methacrylate copolymer, acrylates/C10-30 alkyl acrylate crosspolymer, ammonium polyacryloyldimethyl taurate, sodium polyacrylate, and combinations thereof.

In some embodiments, the pilling-resistant cosmetic composition includes sclerotium gum, acrylamide/sodium acryloyldimethyltaurate copolymer (and) isohexadecane (and) polysorbate 80, or polyacrylate crosspolymer-6, or a combination thereof.

In some embodiments, any one of the least one cosmetically acceptable polymeric thickener is present in a range from about 0.4% to about 3%, by weight, based on the total weight of the pilling-resistant cosmetic composition. In some embodiments, the total amount of the cosmetically acceptable polymeric thickener present in the pilling-resistant cosmetic composition is not more than about 3%, total, by weight, based on the total weight of the pilling-resistant cosmetic composition. In some embodiments, the total amount of polymeric thickener is at least about 0.4%, or at least about 0.5%, or at least about 0.6%, or at least about 0.8%, or at least about 1%, or at least about 1.2%, or at least about 1.5%.

In some embodiments, the total amount of cosmetically acceptable polymeric thickener present in the pilling-resistant cosmetic composition is in an amount from about 0.3% to about 3%, or from about 0.5% to about 2.5%, %, or from about 0.5% to about 2%, or from about 0.6% to about 1.5%, or any suitable combination, sub-combination, range, or sub-range thereof by weight, based on the weight of the pilling-resistant cosmetic composition. One of ordinary skill in the art, however, will appreciate that other ranges are within the scope of the invention.

Thus, each one or the combination of polymers in the pilling-resistant cosmetic composition is present by weight, based on the total weight of the pilling-resistant cosmetic composition, as disclosed above from about 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, to about 3.0 percent, including increments and ranges therein and there between.

Emulsifiers; Ethoxylated Emulsifier Agents (Ethoxylated Agents)

In accordance with the disclosure, a pilling-resistant cosmetic composition according to the disclosure includes at least one ethoxylated agent in liquid form at ambient temperature in a range from about 20° C. to about 28° C. and has an HLB from about 8.5 to about 16.

The term "Hydrophilic-Lipophilic Balance" or "HLB," refers to an empirical expression for the relationship of the hydrophilic and hydrophobic groups of an emulsifier. This term is well known to those skilled in the art. See, e.g., "The HLB system. A time-saving guide to Emulsifier Selection" (Pub: ICI Americas Inc., 1984) and US2006/0217283 at [0053].

In various embodiments, the at least one ethoxylated emulsifier agent has an HLB that is in the range inclusive of from about 8.5 to about 16, for example the ethoxylated emulsifier has an HLB that is in a range from about 8.5, 8.6, 8.7, 8.9, 9, 10, 11, 12, 13, 14, 15, to about 16, including increments of about 0.1 therein and therebetween.

In some embodiments, a pilling-resistant cosmetic composition includes at least one ethoxylated agent in liquid form at ambient temperature in a range from about 20° C. to about 28° C. and has an HLB from about 8.5 to about 16 selected from the group consisting of ethoxylated fatty alcohols, ethoxylated fatty acids, and combinations thereof.

In some embodiments, the at least one ethoxylated agent is selected from the group consisting of laureth-4, oleth-10, and combinations thereof.

In some embodiments, the pilling-resistant cosmetic composition includes one or more ingredients selected from the group consisting of ethoxylated agents selected from laureth-4 and oleth-10, and one or more additional amphiphilic agents selected from polyglyceryl-6 dicaprate, PEG-7 glyceryl cocoate, C14-22 alcohols (and) C12-20 alkyl glucoside, polyglyceryl-4 caprate and combinations thereof, each present in a range from about 0.5% to about 2%, or less that 5%, by weight of the pilling-resistant cosmetic composition.

In some embodiments, the pilling-resistant cosmetic composition includes one or a combination of laureth-4, and one or more additional amphiphilic agents selected from C14-22 alcohols (and) C12-20 alkyl glucoside, polyglyceryl-4 caprate and combinations thereof.

In some embodiments, the at least one ethoxylated agent can include any laureth-x, where x is from 4 to about 12.

In some embodiments, the at least one ethoxylated agent can include any oleth-x, where x is from 5 to about 12.

In some embodiments, the at least one ethoxylated agent can include any PEG-X laurate where X is from 4 to about 12.

In some embodiments, the at least one ethoxylated agent can include any PEG-X isostearate where X is from 5 to about 12.

In some embodiments, the at least one ethoxylated agent can include any PEG-X oleate where X is from 5 to about 12.

In some embodiments, any one of the at least one ethoxylated agent is present in a range from about 0.2% to about 5%, by weight, based on the total weight of the pilling-resistant cosmetic composition. In some embodiments, the total amount of the at least one ethoxylated agent present in the pilling-resistant cosmetic composition is not more than about 5%, total, by weight, based on the total weight of the pilling-resistant cosmetic composition. In some embodiments, the total amount of the at least one ethoxylated agent is at least about 0.4%, or at least about 0.5%, or at least about 0.6%, or at least about 0.8%, or at least about 1%, or at least about 1.2%, or at least about 1.5%.

The amount of the at least one ethoxylated agent present in the pilling-resistant cosmetic composition is provided in a range of from about 0.2% to about 5% by weight, or from about 0.5% to about 3% by weight, or from about 0.8% to about 1.5% or any suitable combination, sub-combination, range, or sub-range thereof by weight, based on the weight of the pilling-resistant cosmetic composition. One of ordinary skill in the art, however, will appreciate that other ranges are within the scope of the invention.

Thus, any one ethoxylated agent or a combination ethoxylated agents are present in the pilling-resistant cosmetic composition, by weight, based on the total weight of the pilling-resistant cosmetic composition, from about 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, to about 5 percent, including increments and ranges therein and there between.

Solvents

Water

In accordance with the various embodiments, water is present in the pilling-resistant cosmetic composition in a range from about 10% to about 95%, or from about 20% to about 85%, or from about 30% to about 80%, or from about 40% to about 75%, or from about 45% to about 65%, or any suitable combination, sub-combination, range, or sub-range thereof by weight, based on the weight of the pilling-resistant cosmetic composition. One of ordinary skill in the art, however, will appreciate that other ranges are within the scope of the invention.

Thus, water may be present by weight, based on the weight of the pilling-resistant cosmetic composition, from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90 to about 95 weight percent, including increments and ranges therein and there between.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the pilling-resistant cosmetic composition is adjusted based on the amount of cosmetically acceptable acid to be in a range from about 4 to about 8, or from about 4.5 to about 7, or from about 5 to about 6 or from about 6 to about 7. The pH is adjusted to the desired value by addition of a base (organic or inorganic), for example sodium hydroxide, potassium hydroxide, or another suitable base, or combinations thereof.

Water-Soluble Solvents

In accordance with some embodiments, the pilling-resistant cosmetic composition may include at least one water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water-soluble solvent has a solubility of at least 60%, 70%, 80%, or 90% in water under these conditions. Non-limiting examples of water-soluble solvents include, for example, glycerin, alcohols (for example, C1-C30, C1-C15, C1-C10, or C1-C4 alcohols), organic solvents, polyols, glycols, or mixtures thereof.

In some embodiments according to the disclosure, when present, a water-soluble solvent may include butylene glycol.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanols (polyhydric alcohols such as glycols and polyols) such as glycerin, 1,2,6-hexanetriol, trimethylolpropane, ethylene glycol, propylene glycol, diethylene glycol, butylene glycol, hexylene glycol, triethylene glycol, tetraethylene glycol, pentaethylene glycol, dipropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, or mixtures thereof.

In accordance with the various embodiments the amount of the at least one water-soluble solvent, when present, is from about 0.1% to about 25%, or from about 0.1% to about 2%, or from about 0.1% to about 1%, or from about 0.1% to about 0.8%, or from about 0.1% to about 0.5%, or from about 1% to about 20%, or from about 1% to about 10%, or from about 2% to about 8%, or any suitable combination, sub-combination, range, or sub-range thereof by weight, based on the weight of the pilling-resistant cosmetic composition. One of ordinary skill in the art, however, will appreciate that other ranges are within the scope of the invention. In some embodiments, the pilling-resistant cosmetic composition includes more than one water soluble solvent, each water-soluble solvent present in an amount as set forth herein above, wherein each different water-soluble solvent may be present within one of the ranges selected from the ranges set forth herein above.

Thus, each one or combination of water-soluble solvents, when present, may be present by weight, based on the total weight of the pilling-resistant cosmetic composition, from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 to about 25 weight percent, including increments and ranges therein and there between.

Oily Phase: Oil

In accordance with the various embodiments, the pilling-resistant cosmetic composition includes at least one oil. The at least one oil is present in the oily phase. In some embodiments, the oily phase also includes one or more of other actives, emulsifiers and oil soluble or solubilizing ingredients distinct from water, water-soluble solvents and water-soluble actives. In some embodiments, the oil is generally immiscible in water. The oil may be selected from hydrocarbons, silicones, fatty alcohols, glycols and vegetable oils. The oil may include one or a combination of polar and non-polar oil. In some embodiments, the oil may be chosen from hydrocarbon-based oils from plants or of plant origin, mineral oil, ester oils, fatty alcohols containing from 12 to 26 carbon atoms, fatty acids containing from 12 to 26 carbon atoms and vinylpyrrolidone copolymers, and combinations thereof.

In accordance with some embodiments, the pilling-resistant cosmetic composition may comprise an emulsion that comprises one or more oils, alone or in combination, with one or more emulsifier (as described herein) wherein the emulsifier is present in an amount that is in the range from about 15% to about 40% of the total amount of oils present in the pilling-resistant cosmetic composition.

In some embodiments according to the disclosure, the at least one oil is selected from the group consisting of octyldodecanol, cetearyl ethylhexanoate (and) isopropyl myristate, hydrogenated lecithin, isononyl isononanoate, isopropyl lauroyl sarcosinate, dicaprylyl carbonate, and combinations thereof.

In some embodiments according to the disclosure, the at least one oil is selected from the group consisting of octyldodecanol, cetearyl ethylhexanoate (and) isopropyl myristate, hydrogenated lecithin, isononyl isononanoate, isopropyl lauroyl sarcosinate, dicaprylyl carbonate, and combinations thereof, wherein octyldodecanol may be present in a range from about 0.5% to about 3.5%, and in some embodiments about 2.4%; and wherein cetearyl ethylhexanoate (and) isopropyl myristate may be present in a range from about 0.5% to about 2%, and in some embodiments about 1.5%; and wherein hydrogenated lecithin may be present in a range from about 0.1% to about 1%, and in some embodiments about 0.3%; and wherein isononyl isononanoate may be present in a range from about 1% to about 5%, and in some embodiments about 2.0%; and wherein isopropyl lauroyl sarcosinate may be present in a range from about 0.5% to about 2%, and in some embodiments about 1.0%; and wherein dicaprylyl carbonate may be present in a range from about 0.5% to about 1.5%, and in some embodiments about 1.0%; all amounts, by weight, based on the weight of the total composition.

In some embodiments the at least one oil comprises a blend of at least two or more of the oils selected from the group consisting of octyldodecanol, cetearyl ethylhexanoate (and) isopropyl myristate, hydrogenated lecithin, isononyl isononanoate, isopropyl lauroyl sarcosinate, dicaprylyl carbonate, and combinations thereof. In some embodiments the at least one oil comprises a blend of at least two or more of the oils selected from the group consisting of octyldodecanol, cetearyl ethylhexanoate (and) isopropyl myristate, hydrogenated lecithin, isononyl isononanoate, isopropyl lauroyl sarcosinate, dicaprylyl carbonate, and combinations thereof.

As used herein, oil refers to any nonpolar compound that is a liquid at 25° C. and is hydrophobic and lipophilic. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa (10-3 to 300 mmHg). The term "non-volatile oil" relates to oil which remains on the skin or the keratin fiber, at room temperature and atmospheric pressure, for at least several hours and which in particular has a vapor pressure of less than 10-3 mmHg (0.13 Pa).

In accordance with the disclosure, by way of non-limiting example, the one or more oil in the pilling-resistant cosmetic composition may be chosen from botanical and essential oils, such as Helianthus Annuus Seed Oil, Lavandula Angustifolia (lavender) Oil, Mentha Piperita Oil, Rosmarinus Officinalis (rosemary) Leaf Oil Pelargonium Graveolens flower oil, Citrus Aurantium Dulcis (orange) peel oil, Menthe Viridis (spearmint) leaf oil, Citrus Aurantifolia (lime) oil, Melaleuca Alternifolia (tea tree) leaf oil, Citrus Grandis (grapefruit) peel oil, Citrus Medica Limonum (lemon) peel oil, rose flower oil, Eucalyptus globulus leaf oil, and combinations thereof.

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

The pilling-resistant cosmetic composition may comprise one or more silicone oils. Non-limiting examples of silicone oils include dimethicone, cyclomethicone, polysilicone-11, phenyl trimethicone, trimethylsilylamodimethicone, and stearoxytrimethylsilane. In some cases, the pilling-resistant cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl) trimethylsiloxysilicates.

Other examples of silicone oils that may be mentioned include volatile linear or cyclic silicone oils, especially those with a viscosity 8 centistokes (8×106 m2/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, hepta methylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The pilling-resistant cosmetic composition may comprise one or more fluoro oils. For example, the one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The pilling-resistant cosmetic composition may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the pilling-resistant cosmetic composition may include a synthetic oil selected from the group consisting of hydrogenated polyisobutene and hydrogenated polydecene. A hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from C4 to C24, it being possible for these chains to be saturated or unsaturated and linear or branched; these oils are in particular wheat germ oil, sunflower oil, grape seed oil, sesame oil, corn oil, apricot oil, castor oil, rhea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ÿ 10, for instance Purcellin oil (cetearyl octanoate), isopropyl myristate, isopropyl palmitate, C12-C15 alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear C12-C13 alkyl) tartrates, such as those sold under the name Cosmacol ETI® by Enichem Augusta Industriale, and also di(linear C14-C15 alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC™ by Cognis;

(viii) fatty amides, such as isopropyl N-lauroyl sarcosinate, such as the product sold under the trade name Eldew SL 205™ from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

Hydrocarbon-based oils may be glyceride triesters and in particular to caprylic/capric acid triglycerides, synthetic esters and in particular isononyl isononanoate, oleyl erucate, C12-C15 alkyl benzoate, 2-ethylphenyl benzoate and fatty alcohols, such as octyldodecanol. As volatile hydrocarbon-based oils, mention is made of hydrocarbon-based oils containing from 8 to 16 carbon atoms and in particular of branched C8-C16 alkanes, such as C8-C16 isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C C8-C16 esters, and isohexyl neopentanoate.

In some embodiments, the pilling-resistant cosmetic composition may comprise one or more oils such as from those described herein above, and from oils that may be selected from branched or linear, liquid alkane with carbon chain length of C11 to C20. In various embodiments, liquid alkanes may be selected from those with a carbon chain length of from C11 to C20. The liquid alkanes may be selected from those with a carbon chain length of from C11 to C20, or from C15 to C19, or one of C11, C12, C13, C14, C15, C16, C17, C18 to C19. In some embodiments, suitable liquid alkanes that may be used according to the disclosure include hydrocarbon-based oils containing from 8 to 16 carbon atoms, and especially branched C8-C16 alkanes such as C8-C16 isoalkanes.

In some embodiments, the pilling-resistant cosmetic composition may comprise one or more oils selected from polar emollients selected from esters, triglycerides, ethers, carbonates, alcohols, oils, butters, fatty acids, and their combinations thereof. In various embodiments, the polar emollients may be selected from those with a molecular weight of 400 g/mol or less. More, generally, the polar emollient may have a molecular weight in the range from about 50 g/mol % to about 350 g/mol.

In some embodiments, the pilling-resistant cosmetic composition may comprise polar emollients that include those derived from C12-C50 fatty acids, preferably C16-C22 saturated fatty acids, and monohydric alcohols. In some embodiments, such esters may be chosen from isopropyl myristate, methyl palmitate, isopropyl laurate, isopropyl palmitate, ethylhexyl palmitate, ethylhexyl laurate, ethylhexyl oleate, ethylhexyl isononanoate, myristyl myristate, 2-ethylhexyl caprate/caprylate (or octyl caprate/caprylate), 2-ethylhexyl palmitate, isostearyl neopentanoate, isononyl isononanoate, hexyl laurate, esters of lactic acid and of fatty alcohols comprising 12 or 13 carbon atoms, dicaprylyl carbonate and their mixtures.

The one or more oil, when present, alone or in combination as a blend of oils, may be present in the pilling-resistant cosmetic composition from about 0.0001% to about 20% or from about 0.001% to about 0.0010%, or from about 0.003% to about 0.004%, or from about 0.01% to about 0.1%, or from about 0.1% to about 10%, or from about 0.5% to about 20%, or from about 1% to about 10%, or from about 5% to about 10%, or from about 2% to about 7%, or from about 0.5% to about 2%, or from about 0.008% to about 0.01%, or from about 0.1% to about 0.2%, or from about 0.5% to about 2%, or from about or any suitable combination, sub-combination, range, or sub-range thereof by weight, based on the weight of the pilling-resistant cosmetic composition. One of ordinary skill in the art, however, will appreciate that other ranges are within the scope of the invention. In some embodiments, the pilling-resistant cosmetic composition includes more than one oil, each oil present in an amount as set forth herein above, wherein each different oil (such as, for example, plant oils and extracts with oils) may be present within one of the ranges selected from the ranges set forth herein above.

Thus, each of the at least one oil or combination of oils is present by weight, based on the total weight of the pilling-resistant cosmetic composition, from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19 to about 20 percent, including increments and ranges therein and there between.

Other Ingredients

In accordance with the various embodiments, each of the oxidizing and chemical peel components of the pilling-resistant cosmetic composition may further include additional ingredients, generally including, but not limited to, chelating agents, pH adjusters, skin actives, humectants, antioxidants, plant extracts, plant oils and butters, fragrances, pearlescent agents, odor absorbers, coloring materials, essential oils, vitamins, antimicrobials and preservatives, and combinations of these. Non limiting examples of some of these optional additional ingredients are provided herein below.

Chelating Agents

In some embodiments, one or more other components, such as chelating agents can be present in the pilling-resistant cosmetic composition, in amounts from about 0.01% to about 2% by weight, from about 0.02% to about 1.5% by weight, from about 0.02% to about 1%, from about 0.02% to about 0.5%, and from about 0.2 to about 0.4%, or any suitable combination, sub-combination, range, or sub-range thereof by weight, based on the weight of the oxidizing component or the pilling-resistant cosmetic composition. In some exemplary embodiments, chelating agents are selected from trisodium ethylenediamine disuccinate, ethylenediaminetetraacetic acid (EDTA), tetrasodium glutamate diacetate, tetrasodium etidronate, tetrasodium pyrophosphate, pentasodium ethylenediamine tetramethylene phosphonate, sodium staminate and combinations of these.

Thus, one or a combination of chelating agents may be present, by weight, based on the total weight of the pilling-resistant cosmetic composition, each one or the combination present from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 up to about 2 weight percent, including increments and ranges therein and there between.

Fillers (Including Powders)

In accordance with some embodiments, the pilling-resistant cosmetic composition may comprise one or more fillers. The fillers may be of mineral or organic origin, natural or synthetic in nature in order to provide oil absorption or optical effects. Oil absorption fillers may impart a matte effect and non-greasy feeling onto the skin. Optical effects fillers may impart a soft-focus/haze/blur effect to the skin, provide the skin with a more uniform appearance, reduce the appearance of skin imperfections or discoloration, or reduce the visibility of pores.

In some particular embodiments, the pilling-resistant cosmetic composition may include fillers in the form of powders. In some embodiments, the pilling-resistant cosmetic composition includes at least one powder selected from the group consisting of silica, pigments, boron nitride, lauroyl lysine, perlite, talc, clays, cellulose, and combinations thereof.

More generally, some examples of oil-absorbing fillers include: mica, zea may (corn) starch, magnesium oxide, nylon-12, nylon-66, cellulose, polyethylene, talc, talc (and) methicone, talc (and) dimethicone, perlite, sodium silicate, pumice, PTFE, Ammonium Polyacryloyldimethyl Taurate, polymethyl methacrylate, oryza sativa (rice) starch, aluminum starch octenylsuccinate, potato starch modified, alumina, calcium sodium borosilicate, magnesium carbonate, hydrated silica, dimethicone/vinyl dimethicone crosspolymer, sodium carboxymethyl starch. According to one preferred embodiment, the oil-absorbing filler comprises spherical microparticles of porous silica having a mean particle size from 0.5 to 20 µm whose INCI name is silica sold by the company JCG Catalysts and Chemicals under the name Spheron L-1500. According to another preferred embodiment, the oil absorbing filler comprises hydrophobic aerogel particles whose INCI name is silica silylate sold by Dow Corning under the name VM-2270 Aerogel Fine Particles.

Some examples of optical effects fillers include: bismuth oxychloride, silica silylate, boron nitride, iron oxide, calcium carbonate, calcium sulfate (and) iron oxides, sodium potassium aluminum silicate.

Some examples of fillers which provide both oil-absorbing and optical effects include: silica, silica (and) methicone, silica (and) dimethicone, polysilicone-22, polysilicone-8, polysilicone-11, methyl methacrylate crosspolymer, polymethylsilsesquioxane, methylsilanol/silicate crosspolymer, vinyl dimethicone/methicone silsesquioxane crosspolymer, diphenyl dimethicone/vinyl diphenyl dimethicone silsesquioxane crosspolymer, and styrene/acrylates copolymer.

The filler, for example a powder, may be present in the pilling-resistant cosmetic composition according to the invention, at a concentration, or from about 0.01% to 25%, or from about 0.01% to 0.5%, or from about 0.1% to 0.4%, or from about 0.2% to 0.3%, or from about 0.5% to 5.0%, or from about 1.0% to 5.0%, or from about 1.2% to 3.5%, or from about 1.0% to 2.5%, or from about 1.5% to about 2%, or from about 1.0% to about 1.8%, or from about 2.2% to about 2.7% or from about 0.25% to about 0.4%, or any suitable combination, sub-combination, range, or sub-range thereof by weight, based on the weight of the pilling-resistant cosmetic composition. One of ordinary skill in the art, however, will appreciate that other ranges are within the scope of the invention. In some embodiments, the pilling-resistant cosmetic composition includes more than one filler, each filler present in an amount as set forth herein above, wherein each different filler may be present within one of the ranges selected from the ranges set forth herein above.

Thus, each one or combination of filler, when present, may be present by weight, based on the total weight of the pilling-resistant cosmetic composition, from about 0.01, 0.02, 0.03, 0.04, 0.05, 0.06, 0.07, 0.08, 0.09, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0 to about 25.0 percent by weight, including increments and ranges there between.

Optional Actives and Other Ingredients

In some embodiments, there may be one or more optional actives or other ingredients (herein, "additives") present in the pilling-resistant cosmetic composition, the one or more additives selected from, for example, but not limited to: humectants, such as acetamide MEA, glycols, such as glycerin and propylene glycol; anti-microbials; antioxidants, including, but not limited to, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (Scutellaria Baicalensis root extract), pine bark extract (Pinus Pinaster bark/bud extract), ellagic acid; hyaluronic acid and its derivatives; hydroxyacetophenone; and vitamins and vitamin derivatives, such as tocopherol and ascorbic acid; and combinations thereof.

In some embodiments, additives may include one or a combination of antimicrobial agents and their salts, for example, including, but not limited to, the group consisting of chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, and pentylene glycol, and combinations thereof.

In some embodiments, additives may include one or a combination of skin actives, for example, including, but not limited to, the group consisting of additional emulsifiers not otherwise excluded (for example, polysaccharide emulsifiers, such as inulin lauryl carbamate), tocopherol, niacinamide, phenoxyethanol, sodium hyaluronate, capryloyl salicylic acid, phenylethyl resorcinol, hydroxyacetophenone, and combinations thereof.

In some embodiments, the one or more additives present in the pilling-resistant cosmetic composition may include one or more other components, for example, including, but not limited to, the group consisting of penetrants; sequestrants; fragrances; dispersants; ceramides; opacifiers and combinations thereof. Although the aforementioned optional components are given as an example, it will be appreciated that other optional components compatible with cosmetic applications known in the art may be used.

In accordance with the various embodiments, the amounts of additives, for example, actives and other components, present in the pilling-resistant cosmetic composition can range from about 0.001% to about 50%, from about 0.5% to about 30%, from about 1.5% to about 20%, and from about 5% to about 15%, or any suitable combination, sub-combination, range, or sub-range thereof by weight, based on the weight of the oxidizing component or the pilling-resistant cosmetic composition.

In some embodiments, one or more additives, alone or in combination, can be present in one or both of the oxidizing component and the pilling-resistant cosmetic composition from about 0.05% to about 50% by weight, from about 0.05% to about 2.5% by weight, from about 0.1% to about 2%, from about 0.25% to about 1.5%, and from about 0.5% to about 1.25%, or any suitable combination, sub-combination, range, or sub-range thereof by weight, based on the weight of the pilling-resistant cosmetic composition.

In some embodiments, one or more other components, such as preservatives, vitamins, preservatives, and the like, alone or in combination, can be present in one or both of the oxidizing component and the pilling-resistant cosmetic composition from about 0.05% to about 50% by weight, from about 0.05% to about 25% by weight, from about 0.1% to about 10%, from about 0.25% to about 5%, and from about 0.5 to about 3.5%, or any suitable combination, sub-combination, range, or sub-range thereof by weight, based on the weight of the pilling-resistant cosmetic composition.

Thus, one or a combination of additives may be present in the pilling-resistant cosmetic composition, by weight, based on the weight of the oxidizing component or the pilling-resistant cosmetic composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0 0.80, 0.90, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

EXAMPLES

Example 1: Raw Materials

The following raw materials were used in the examples herein.

TABLE 1

Raw Materials

| Raw Material | Percent Active (approximate, based on RM supplier) |
|---|---|
| Polyacrylate Crosspolymer-6 (Sepimax Zen (TM)) | ~100% |
| Xanthan Gum | ~100% |
| HYDROXYETHYL ACRYLATE/SODIUM ACRYLOYLDIMETHYL TAURATE COPOLYMER (Sepinov (TM) EMT-10) | ~100% |
| ACRYLAMIDE/SODIUM ACRYLOYL-DIMETHYLTAURATE COPOLYMER (Simulgel (TM) 600) | ~100% |
| Carbomer (SYNTHALEN (TM) K) | ~100% |
| AMMONIUM ACRYLOYLDIMETHYL-TAURATE/STEARETH-25 METHACRYLATE CROSSPOLYMER (Aristoflex (TM) HMS) | ~40% |
| AMMONIUM POLYACRYLOYL-DIMETHYL TAURATE (Hostacerin (TM) AMPS) | ~100% |
| Sodium Polyacrylate (COSMEDIA (TM) SP | ~100% |
| Inulin lauryl carbamate | ~25% (balance glycerin) |
| TRISODIUM ETHYLENEDIAMINE DISUCCINATE | ~37% (balance water) |

Example 2: In Vitro Evaluation of Pilling

A simplex oil in water emulsion was made (BASE, as shown in TABLE 2), and a variety of polymeric thickeners were each added with water and with one of each of water control and a variety of amphiphilic liquid RM with HLB 8.5-16, including formulations containing one or more ethoxylated agents according to the disclosure to make 40 discrete test formulas. In each instance, the final concentration of polymeric thickener was in an amount known to produce pilling.

The test protocol for in vitro pilling is as follows:

Test protocol using Skin FX:
a. Heat a sheet of BioSkin to 35 C on a controlled hot plate.
b. Apply 0.1 mL of a formula to a small area of BioSkin.
c. Rub product in with 15 circular motions in 15 seconds.
d. Wait 15 seconds.
e. Once again, rub product in with 15 circular motions in 15 seconds.
f. Wait 2.5 min.
g. Quickly rub area where product was applied 5 times.
h. Note any pilling.
i. Repeat for all formulas in a different area of BioSkin.

TABLE 2

BASE Formulation

| INGREDIENT | % Ingredients in Final Test Formulation |
|---|---|
| Water | QS |
| Glycerin | 7 |
| Chlorphenesin | 0.2 |
| Phenoxyethanol | 0.8 |
| Polysorbate 20 | 1 |
| Isononyl Isononanoate | 2 |
| Caprylic/capric Triglycerides | 2 |
| Amphiphilic liquid RM with HLB 8.5-16 (see TABLE 4 for specific EA used) | (1) |
| Polymeric Thickener (see TABLES 3 and 5 for specific PT used and amount) | See TABLE 2 |

TABLE 3

Polymeric Thickeners (PT) Used in Test Formulations

| Polymer | Ingredient | % in Final Test Formulation |
|---|---|---|
| A | polyacrylate crosspolymer-6 | 1.5 |
| B | xanthan gum | 1.3 |
| C | hydroxyethyl acrylate/sodium acryloyldimethyl taurate copolymer | 1.3 |
| D | acrylamide/sodium acryloyldimethyltaurate copolymer* | 5.0 |
| E | carbomer | 0.8 + 0.3 NaOH |
| F | ammonium acryloyldimethyltaurate/steareth-25 methacrylate crosspolymer | 1.1 |
| G | ammonium polyacryloyldimethyl taurate | 1.3 |
| H | sodium polyacrylate | 1.3 |

*Given in % RM, not % active; 5% RM = 2% active polymer

TABLE 4

Amphiphilic liquid RM with HLB 8.5-16 Used in Test Formulations

| Amphiphilic liquid RM with HLB 8.5-16 | % in Final Test Formulation |
|---|---|
| laureth-4 | 1 |
| polyglyceryl-6 dicaprate | 1 |
| oleth-10 | 1 |
| PEG-7 glyceryl cocoate | 1 |

Each emulsifier was added separately to each 'control' formula above. Then, the pilling test was repeated, and results were evaluated.

TABLE 5

Pilling in Vitro Test Results

| Amphiphilic liquid RM with HLB 8.5-16 | Polymeric Thickener | | | | | | | |
|---|---|---|---|---|---|---|---|---|
| | A | B | C | D | E | F | G | H |
| None | SP | SP | SP | SP | SP | SP | SP | SP |
| laureth-4 | NP | NP | NP | NP | NP | NP | NP | NP |
| polyglyceryl-6 dicaprate | NP | SP | NP | NP | NP | SP | NP | NP |
| oleth-10 | NP | MP | NP | NP | NP | NP | NP | NP |
| PEG-7 glyceryl cocoate | SP | SP | NP | NP | NP | SP | NP | NP |

TABLE 5 shows the in vitro pilling test results with each of the test formulas. NP=no pilling, MP=minimal pilling and SP=significant pilling.

As shown in TABLE 5, each of laureth-4 and oleth-10 prevented pilling in with all eight tested polymeric thickeners. The formulations including only amphiphilic liquid RM with HLB 8.5-16 (i.e., without any ethoxylated agent) did not fully eliminate pilling when used with two of the eight polymeric thickeners, and likewise, the PEG glyceryl cocoate amphiphilic liquid RM with HLB 8.5-16 (i.e., without any ethoxylated agent) did not fully eliminate pilling when used with three of the eight polymeric thickeners. Each of laureth and oleth forms of ethoxylated agents, each being linear ethoxylated fatty alcohols (each containing only 1 —OH or —COOH present in starting alcohol or acid), fully eliminated pilling with all of polymeric thickeners. In contrast, each of the polyglyceryl and PEG glyceryl cocoate forms are non-linear amphiphilic liquid RM with HLB 8.5-16 and structurally dissimilar from the EAs employed in the study, did not beneficially diminish or eliminate pilling.

Example 3: Representative Inventive Composition

The following inventive and comparative compositions are within the scope of the disclosure

TABLE 6

Inventive and Comparative Compositions

| INGREDIENT | INVENTIVE 1 | INVENTIVE 2 | COMPARATIVE |
|---|---|---|---|
| OIL BLEND (OCTYLDODECANOL, HYDROGENATED LECITHIN, ISONONYL ISONONANOATE, ISOPROPYL LAUROYL SARCOSINATE, DICAPRYLYL CARBONATE, CETEARYL | 8.2 | 8.2 | 8.2 |

TABLE 6-continued

Inventive and Comparative Compositions

| INGREDIENT | INVEN-TIVE 1 | INVEN-TIVE 2 | COMPAR-ATIVE |
|---|---|---|---|
| ETHYLHEXANOATE (AND) ISOPROPYL MYRISTATE)) | | | |
| SODIUM HYDROXIDE | 0.22 | 0.22 | 0.22 |
| ACTIVES/ADDITIVES (TOCOPHEROL, SALICYLIC ACID, NIACINAMIDE, PHENOXYETHANOL, INULIN LAURYL CARBAMATE, CAPRYLOYL SALICYLIC ACID, other additives) | 16.1 | 16.1 | 16.1 |
| LAURETH-4 | 1.0 | 0.5 | 0.5 |
| BUTYLENE GLYCOL | 5.4 | 5.4 | 5.4 |
| WATER | 55.48 | 56.78 | 56.78 |
| LAUROYL LYSINE | 0.4 | 0.4 | 0.4 |
| SCLEROTIUM GUM | 0.2 | 0.2 | 0.2 |
| BORON NITRIDE | 0.4 | 0.4 | 0.4 |
| ACRYLAMIDE/SODIUM ACRYLOYLDIMETHYL-TAURATE COPOLYMER (and) ISOHEXADECANE (and) POLYSORBATE 80 | 1.0 | 1.0 | 1.0 |
| C14-22 ALCOHOLS (and) C12-20 ALKYL GLUCOSIDE | 1.5 | 1.5 | 1.5 |
| ETHOXYDIGLYCOL | 2.6 | 2.6 | 2.6 |
| POLYGLYCERYL-4 CAPRATE | 1.8 | 1. | 1. |
| TRISODIUM ETHYLENEDIAMINE DISUCCINATE | 0.3 | 0.3 | 0.3 |
| POLYACRYLATE CROSSPOLYMER-6 | 0.7 | 0.7 | 0.7 |
| HYDROXYACETOPHENONE | 0.5 | 0.5 | 0.5 |
| SILICONES (DIMETHICONE (and) DIMETHICONOL, DIMETHICONE (and) POLYSILICONE-11) | 4.2 | 4.2 | 4.2 |

Example 4: In Vivo Evaluation of Pilling

To demonstrate the benefit of the inventive composition in vivo, inventive and a comparative formulation (lacking emulsifier) were tested for pilling on human subjects according to a protocol similar to the in vitro test described above. The ethoxylated emulsifier agent included in the comparative formulations was laureth-4, present at 0% (comparative/baseline), 0.5% and 1% (inventives).

The results revealed that on human subjects, the formula with the most laureth-4 (1%) showed the least amount of pilling. The formula with no laureth-4 showed the most pilling. The formula with the lowest amount of laureth-4 (0.5%) showed intermediate pilling, but was improved over the baseline.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising," "consisting essentially of," and "consisting of," when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. A pilling-resistant cosmetic composition in the form of an oil in water emulsion comprising a water phase and an oily phase, the pilling-resistant cosmetic composition comprising:
   (i) at least one cosmetically acceptable polymeric thickener selected from the group consisting of polyacrylate crosspolymer-6, xanthan gum, hydroxyethyl acrylate/sodium acryloyldimethyl taurate copolymer, acrylamide/sodium acryloyldimethyltaurate copolymer, carbomer, ammonium acryloyldimethyltaurate/steareth-25 methacrylate crosspolymer, ammonium polyacryloyldimethyl taurate, sodium polyacrylate, sclerotium gum, acrylamide/sodium acryloyldimethyltaurate copolymer and isohexadecane and polysorbate 80, and combinations thereof, present in a total amount in a range from about 0.4% to about 2.5%, by weight, based on the total weight of the pilling-resistant cosmetic composition;
   (ii) at least one ethoxylated agent selected from the group consisting of laureth-4, oleth-10, and combinations thereof, present in a total amount of ethoxylated agent in a range from about 0.2% to about 2%, by weight, based on the total weight of the pilling-resistant cosmetic composition; and
   (iii) at least one oil including at least one oil component selected from the group consisting of octyldodecanol, glycine soja (soybean) oil, hydrogenated lecithin, cetearyl ethylhexanoate (and) isopropyl myristate, isononyl isononanoate, isocetyl stearoyl stearate, dicaprylyl ether, isopropyl lauroyl sarcosinate, dicaprylyl carbonate, isohexadecane, isodecane, isododecane, and combinations thereof,
   wherein the pilling-resistant cosmetic composition resists pilling when applied by rubbing or smoothing on a keratinous substrate,
   wherein the pilling-resistant cosmetic composition is free of additives other than 1,2-hexandiol, 3-heptoyl-2,2-propandiol, 4-hydroxyacetophenone alkylphenols, alumina, aluminum starch octenylsuccinate, ammonium polyacryloyldimethyl taurate, anthocyanidins, antimicrobials, antioxidants, ascorbic acid, aurones, baicalin, benzalkonium chloride, benzoic acid, benzyl alcohol, benzylglycerin, betacyanins, bismuth oxychloride, boron nitride, caffeic acid, calcium carbonate, calcium sodium borosilicate, calcium sulfate, caprylhydroxamic acid, caproyl salicylic acid, caprylyl glycol, capsacinoids, catechins, cellulose, ceramides, chalcones, chelating agents, chlorphenesin, cinnamic acid, clays, coloring materials, curcumin, curcuminoids, dihydroflavonols, dimethicone, dimethicone/vinyl dimethicone crosspolymer, diphenyl dimethicone/vinyl diphenyl dimethicone silsesquioxane crosspolymer, dispersants, ellagic acid, emulsifiers, essential oils, ethylhexylglycerin, ferulic acid, fillers, flavanols, flavanones, flavones, flavonols, fragrances, glycerin, glycols, hexyl glycerin, humectants, hyaluronic acid and its derivatives, hydrated silica, hydrophobic aerogel particles, hydroxyacetophenone, hydroxybenzoketones, hydroxytyrosol, inulin lauryl carbamate, iron oxides, isoflavonoids, lauroyl lysine, lignans, magnesium carbonate, magnesium oxide, MEA, methicone, methoxyphenols, methyl methacrylate crosspolymer, methylsilanol/silicate crosspolymer, mica, naphthoquinones, neoflavonoids, niacinamide, nylon-12, nylon-66, octylglycerin, odor absorbers, oil-absorbing fillers, opacifiers, oryza sativa rice starch, p-coumaric acid, pearlescent agents, penetrants, pentylene glycol, perlite, pH adjusters, phenethyl alcohol, phenolic compounds, phenolic terpenes, phenoxyethanol, phenylethyl resorcinol, pigments, pine bark extract, pinoresinol, piroctone olamine, plant butters, plant extracts, plant oils, polyethylene, polymethyl methacrylate, polymethylsilsesquioxane, polysaccharide emulsifiers, polysilicone-11, polysilicone-22, polysilicone-8, potato starch modified, preservatives, propylene glycol, PTFE, pumice, resveratrol, salicylic acid, sequestrants, silica, silica silylate, sodium carboxymethyl starch, sodium hyaluronate, sodium potassium aluminum silicate, sodium silicate, stilbenoids, styrene/acrylates copolymer, talc, tannins, tocopherol, trisodium ethylenediamine disuccinate, vinyl dimethicone/methicone silsesquioxane crosspolymer, vitamins, vitamin derivatives, zea may corn starch, salts thereof, and combinations thereof, and
   wherein the antimicrobials are selected from the group consisting of chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, pentylene glycol, salts thereof, and combinations thereof.

2. The pilling-resistant cosmetic composition according to claim 1, wherein the at least one ethoxylated agent includes the oleth-10.

3. The pilling-resistant cosmetic composition according to claim 1, wherein the at least one oil is selected from the group consisting of octyldodecanol, glycine soja (soybean) oil, hydrogenated lecithin, cetearyl ethylhexanoate (and) isopropyl myristate, isononyl isononanoate, isocetyl stearoyl stearate, dicaprylyl ether, isopropyl lauroyl sarcosinate, dicaprylyl carbonate, and combinations thereof.

4. The pilling-resistant cosmetic composition according to claim 1, wherein the at least one oil is selected from the group consisting of octyldodecanol present in a range from about 0.5% to about 3.5; cetearyl ethylhexanoate (and) isopropyl myristate present in a range from about 0.5% to about 2%; hydrogenated lecithin present in a range from about 0.1% to about 1%; isononyl isononanoate present in a range from about 1% to about 5%; isopropyl lauroyl sarcosinate present in a range from about 0.5% to about 2%; dicaprylyl carbonate present in a range from about 0.5% to about 1.5%; and combinations thereof, all amounts, by weight, based on the weight of the total composition.

5. The pilling-resistant cosmetic composition according to claim 1, wherein the at least one oil is selected from the group consisting of octyldodecanol present at about 2.4%; cetearyl ethylhexanoate (and) isopropyl myristate present at about 1.5%; hydrogenated lecithin present at about 0.3%; isononyl isononanoate present at about 2.0%; isopropyl lauroyl sarcosinate present at about 1.0%; dicaprylyl carbonate present at about 1.0%; and combinations thereof, all amounts, by weight, based on the weight of the total composition.

6. The pilling-resistant cosmetic composition according to claim 1, further comprising one or more ingredients selected from the group consisting of water-soluble solvents, at least one powder present in either the water or the oily phase, one or more additives present in either the water or the oily phase, and combinations thereof.

7. The pilling-resistant cosmetic composition according to claim 6, comprising at least one powder, wherein the at least one powder is selected from the group consisting of silica, pigments, boron nitride, lauroyl lysine, perlite, talc, clays, cellulose, and combinations thereof.

8. The pilling-resistant cosmetic composition according to claim 1, wherein the water phase is present in an amount that is at least about 40% or more, based on the total weight of the pilling-resistant composition.

9. The pilling-resistant cosmetic composition according to claim 1, wherein the oily phase is present in an amount that is not greater than about 40%, based on the total weight of the pilling-resistant composition.

10. The pilling-resistant cosmetic composition according to claim 1, wherein the ethoxylated agent comprises laureth-4, the pilling-resistant cosmetic composition further comprising C14-22 alcohols (and) C12-20 alkyl glucoside.

11. The pilling-resistant cosmetic composition according to claim 1, wherein the at least one ethoxylated agent is in liquid form at an ambient temperature of about 25° C.

12. The pilling-resistant cosmetic composition according to claim 1, wherein the pilling-resistant cosmetic composition is free of glyceride triesters and hydrogenated polyisobutene.

13. A pilling-resistant cosmetic composition in the form of an oil in water emulsion, comprising:
  (i) at least one polymeric thickener selected from the group consisting of polyacrylate crosspolymer-6, xanthan gum, hydroxyethyl acrylate/sodium acryloyldimethyl taurate copolymer, acrylamide/sodium acryloyldimethyltaurate copolymer, carbomer, ammonium acryloyldimethyltaurate/steareth-25 methacrylate crosspolymer, acrylates/beheneth-25 methacrylate copolymer, acrylates/C10-30 alkyl acrylate crosspolymer, ammonium polyacryloyldimethyl taurate, sodium polyacrylate, sclerotium gum, acrylamide/sodium acryloyldimethyltaurate copolymer (and) isohexadecane (and) polysorbate 80, and combinations thereof, present in a total amount in a range from about 0.4% to about 2.5%, by weight, based on the total weight of the pilling-resistant cosmetic composition;
  (ii) at least one ethoxylated agent in liquid form at ambient temperature in a range from about 20° C. to about 28° C. and has an HLB from about 8.5 to about 16, present in a total amount of ethoxylated agent in a range from about 0.2% to about 2%, by weight, based on the total weight of the pilling-resistant cosmetic composition; and
  (iii) at least one oil including at least one oil component selected from the group consisting of octyldodecanol, glycine soja (soybean) oil, hydrogenated lecithin, cetearyl ethylhexanoate (and) isopropyl myristate, isononyl isononanoate, isocetyl stearoyl stearate, dicaprylyl ether, isopropyl lauroyl sarcosinate, dicaprylyl carbonate, isohexadecane, isodecane, isododecane, and combinations thereof,
  wherein the pilling-resistant cosmetic composition resists pilling when applied by rubbing or smoothing on a keratinous substrate,
  wherein the pilling-resistant cosmetic composition is free of additives other than 1,2-hexandiol, 3-heptoyl-2,2-propandiol, 4-hydroxyacetophenone alkylphenols, alumina, aluminum starch octenylsuccinate, ammonium polyacryloyldimethyl taurate, anthocyanidins, antimicrobials, antioxidants, ascorbic acid, aurones, baicalin, benzalkonium chloride, benzoic acid, benzyl alcohol, benzylglycerin, betacyanins, bismuth oxychloride, boron nitride, caffeic acid, calcium carbonate, calcium sodium borosilicate, calcium sulfate, caprylhydroxamic acid, capryloyl salicylic acid, caprylyl glycol, capsacinoids, catechins, cellulose, ceramides, chalcones, chelating agents, chlorphenesin, cinnamic acid, clays, coloring materials, curcumin, curcuminoids, dihydroflavonols, dimethicone, dimethicone/vinyl dimethicone crosspolymer, diphenyl dimethicone/vinyl diphenyl dimethicone silsesquioxane crosspolymer, dispersants, ellagic acid, emulsifiers, essential oils, ethylhexylglycerin, ferulic acid, fillers, flavanols, flavanones, flavones, flavonols, fragrances, glycerin, glycols, hexyl glycerin, humectants, hyaluronic acid and its derivatives, hydrated silica, hydrophobic aerogel particles, hydroxyacetophenone, hydroxybenzoketones, hydroxytyrosol, inulin lauryl carbamate, iron oxides, isoflavonoids, lauroyl lysine, lignans, magnesium carbonate, magnesium oxide, MEA, methicone, methoxyphenols, methyl methacrylate crosspolymer, methylsilanol/silicate crosspolymer, mica, naphthoquinones, neoflavonoids, niacinamide, octylglycerin, odor absorbers, oil-absorbing fillers, opacifiers, oryza sativa rice starch, p-coumaric acid, pearlescent agents, penetrants, pentylene glycol, perlite, pH adjusters, phenethyl alcohol, phenolic compounds, phenolic terpenes, phenoxyethanol, phenylethyl resorcinol, pigments, pine bark extract, pinoresinol, piroctone olamine, plant butters, plant extracts, plant oils, polyethylene, polymethyl methacrylate, polymethylsilsesquioxane, polysaccharide emulsifiers, polysilicone-11, polysilicone-22, polysilicone-8, potato starch modified, preservatives, propylene glycol, PTFE, pumice, resveratrol, salicylic acid, sequestrants, silica, silica silylate, sodium carboxymethyl starch, sodium hyaluronate, sodium potassium aluminum silicate, sodium silicate, stilbenoids, styrene/acrylates copolymer, talc, tannins, tocopherol, trisodium ethylenediamine disuccinate, vinyl dimethicone/methicone silsesquioxane crosspolymer, vitamins, vitamin derivatives, zea may corn starch, salts thereof, and combinations thereof, and
  wherein the antimicrobials are selected from the group consisting of chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, pentylene glycol, salts thereof, and combinations thereof.

14. The pilling-resistant cosmetic composition according to claim 13, wherein the at least one ethoxylated agent is selected from the group consisting of ethoxylated fatty alcohols, ethoxylated fatty acids, and combinations thereof.

15. The pilling-resistant cosmetic composition according to claim 13, wherein the at least one ethoxylated agent is selected from the group consisting of (i) an laureth-x, where x is from 4 to about 12; (ii) an oleth-x, where x is from 5 to about 12; (iii) an PEG-X laurate where X is from 4 to about 12; (iv) an PEG-X isostearate where X is from 5 to about 12; (v) an PEG-X oleate where X is from 5 to about 12; and combinations thereof.

16. The pilling-resistant cosmetic composition according to claim 13, wherein the at least one ethoxylated agent is selected from the group consisting of laureth-4, oleth-10, and combinations thereof.

17. A pilling-resistant cosmetic composition in the form of an oil in water emulsion, comprising:
(i) at least one cosmetically acceptable polymeric thickener selected from the group consisting of:
crosspolymers;
gums;
taurate based polymers;
carbomers;
polyacrylates selected from the group consisting of polyacrylate crosspolymer-6, acrylates/beheneth-25 methacrylate copolymer, acrylates/C10-30 alkyl acrylate crosspolymer, sodium polyacrylate, and combinations thereof; and
combinations thereof, and
present in a total amount of polymeric thickener in a range from about 0.4% to 2%, by weight, based on the total weight of the pilling-resistant cosmetic composition;
(ii) at least one ethoxylated agent in liquid form at ambient temperature in a range from about 20° C. to about 28° C. and has an HLB from about 8.5 to about 16, present in a total amount or ethoxylated agent in a range from about 0.2% to about 2%, by weight, based on the total weight of the pilling-resistant cosmetic composition; and
(iii) at least one oil including at least one oil component selected from the group consisting of octyldodecanol, glycine soja (soybean) oil, hydrogenated lecithin, cetearyl ethylhexanoate (and) isopropyl myristate, isononyl isononanoate, isocetyl stearoyl stearate, dicaprylyl ether, isopropyl lauroyl sarcosinate, dicaprylyl carbonate, isohexadecane, isodecane, isododecane, and combinations thereof,
wherein the pilling-resistant cosmetic composition resists pilling when applied by rubbing or smoothing on a keratinous substrate,
wherein the pilling-resistant cosmetic composition is free of additives other than 1,2-hexandiol, 3-heptoyl-2,2-propandiol, 4-hydroxyacetophenone alkylphenols, alumina, aluminum starch octenylsuccinate, ammonium polyacryloyldimethyl taurate, anthocyanidins, antimicrobials, antioxidants, ascorbic acid, aurones, baicalin, benzalkonium chloride, benzoic acid, benzyl alcohol, benzylglycerin, betacyanins, bismuth oxychloride, boron nitride, caffeic acid, calcium carbonate, calcium sodium borosilicate, calcium sulfate, caprylhydroxamic acid, caprylyl salicylic acid, caprylyl glycol, capsacinoids, catechins, cellulose, ceramides, chalcones, chelating agents, chlorphenesin, cinnamic acid, clays, coloring materials, curcumin, curcuminoids, dihydroflavonols, dimethicone, dimethicone/vinyl dimethicone crosspolymer, diphenyl dimethicone/vinyl diphenyl dimethicone silsesquioxane crosspolymer, dispersants, ellagic acid, emulsifiers, essential oils, ethylhexylglycerin, ferulic acid, fillers, flavanols, flavanones, flavones, flavonols, fragrances, glycerin, glycols, hexyl glycerin, humectants, hyaluronic acid and its derivatives, hydrated silica, hydrophobic aerogel particles, hydroxyacetophenone, hydroxybenzoketones, hydroxytyrosol, inulin lauryl carbamate, iron oxides, isoflavonoids, lauroyl lysine, lignans, magnesium carbonate, magnesium oxide, MEA, methicone, methoxyphenols, methyl methacrylate crosspolymer, methylsilanol/silicate crosspolymer, mica, naphthoquinones, neoflavonoids, niacinamide, nylon-12, nylon-66, octylglycerin, odor absorbers, oil-absorbing fillers, opacifiers, oryza sativa rice starch, p-coumaric acid, pearlescent agents, penetrants, pentylene glycol, perlite, pH adjusters, phenethyl alcohol, phenolic compounds, phenolic terpenes, phenoxyethanol, phenylethyl resorcinol, pine bark extract, pinoresinol, piroctone olamine, plant butters, plant extracts, plant oils, polyethylene, polymethyl methacrylate, polymethylsilsesquioxane, polysaccharide emulsifiers, polysilicone-11, polysilicone-22, polysilicone-8, potato starch modified, preservatives, propylene glycol, PTFE, pumice, resveratrol, salicylic acid, sequestrants, silica, silica silylate, sodium carboxymethyl starch, sodium hyaluronate, sodium potassium aluminum silicate, sodium silicate, stilbenoids, styrene/acrylates copolymer, talc, tannins, tocopherol, trisodium ethylenediamine disuccinate, vinyl dimethicone/methicone silsesquioxane crosspolymer, vitamins, vitamin derivatives, zea may corn starch, salts thereof, and combinations thereof, and
wherein the antimicrobials are selected from the group consisting of chlorphenesin, caprylyl glycol, phenoxyethanol, caprylhydroxamic acid, benzoic acid, salicylic acid, benzyl alcohol, phenethyl alcohol, benzalkonium chloride, 4-hydroxyacetophenone, piroctone olamine, hexyl glycerin, ethylhexylglycerin, octylglycerin, benzylglycerin, 3-heptoyl-2,2-propandiol, and 1,2-hexandiol, pentylene glycol, salts thereof, and combinations thereof.

18. The pilling-resistant cosmetic composition according to claim 17, wherein the at least one cosmetically acceptable polymeric thickener is a gum selected from the group consisting of sclerotium gum, xanthan gum, cellulose gum, locust bean gum, carrageenan, and combinations thereof.

19. The pilling-resistant cosmetic composition according to claim 17, wherein the at least one cosmetically acceptable polymeric thickener is selected from the group consisting of xanthan gum, hydroxyethyl acrylate/sodium acryloyldimethyl taurate copolymer, acrylamide/sodium acryloyldimethyltaurate copolymer, carbomer, ammonium acryloyldimethyltaurate/steareth-25 methacrylate crosspolymer, ammonium polyacryloyldimethyl taurate, sclerotium gum, acrylamide/sodium acryloyldimethyltaurate copolymer (and) isohexadecane (and) polysorbate 80, and combinations thereof.

20. The pilling-resistant cosmetic composition according to claim 17, wherein the at least one ethoxylated agent is selected from the group consisting of (i) an laureth-x, where x is from 4 to about 12; (ii) an oleth-x, where x is from 5 to about 12; (iii) an PEG-X laurate where X is from 4 to about 12; (iv) an PEG-X isostearate where X is from 5 to about 12; (v) an PEG-X oleate where X is from 5 to about 12; and combinations thereof.

* * * * *